United States Patent [19]
Hillman et al.

[11] Patent Number: 5,858,675
[45] Date of Patent: Jan. 12, 1999

[54] DOUBLE-STRANDED RNA-BINDING PROTEIN

[75] Inventors: Jennifer L. Hillman, Mountain View; Preeti Lal, Sunnyvale; Neil C. Corley, Mountain View, all of Calif.

[73] Assignee: Incyte Pharmaceuticals, Inc., Palo Alto, Calif.

[21] Appl. No.: 855,518

[22] Filed: May 13, 1997

[51] Int. Cl.$^6$ .............................. C12Q 1/68; C12P 19/34; C07H 21/02; C07H 21/04

[52] U.S. Cl. ..................... 435/6; 435/91.2; 435/320.1; 435/240.2; 435/252.3; 536/23.1; 536/24.3; 536/24.31; 536/24.33

[58] Field of Search ........................... 435/6, 91.2, 320.1, 435/240.2, 252.3; 536/23.1, 24.3, 24.31, 24.32, 24.33

[56] References Cited

PUBLICATIONS

S. Palmer genbank record (publicly available Jan. 22, 1997) Genbank Accession record Z84477, (submitted Nov. 6, 1996), Jan. 1997.

Hillier et al genbank record (publicly available Apr. 02, 1996) Genbank Accession record N76259, (submitted 1995), Apr. 1996.

Sambrook et al (Molecular Cloning: A Laboratory Manual, Cold Spring Harbor Laboratory Press, Cold Spring Harbor, New York) page 17.2, 1989.

Burd, C.G. et al., "Conserved Structures and Diversity of Functions of RNA–Binding Proteins", *Science*, 265: 615–621 (1994).

St. Johnston, D. et al., "A conserved double–stranded RNA–binding domain", *Proc. Natl. Acad. Sci.*, 89: 10979–10983 (1992).

Gatignol, A. et al., "Sequential Steps in Tat Trans–Activation of HIV–1 Mediated Through Cellular DNA, RNA, and Protein Binding Factors", *Gene Expression*, 5: 217–228 (1996).

Benkirane, M. et al., "Oncogenic potential of TAR RNA binding protein TRBP and its regulatory interaction with RNA–dependent protein kinase PKR", *EMBO J.*, 16: 611–624 (1997).

Lee, K. et al., "A Testis Cytoplasmic RNA–Binding Protein That Has the Properties of a Translational Repressor", *Mol. Cell. Biol.*, 16: 3023–3034 (1996) (GI 1737216).

Jantsch, M.F. et al., (Direct Submission), GenBank Sequence Database (Accession M96370), National Center for Biotechnology Information, National Library of Medicine, Bethesda, Maryland, 20894 (GI 214738) (GI 214739) (1992).

Gatignol, A. et al., (Direct Submission), GenBank Sequence Database (Accession U08998), National Center for Biotechnology Information , National Library of Medicine, Bethesda, Maryland, 20894 (GI 478989) (GI 478990) (1997).

*Primary Examiner*—Jeffrey Fredman
*Attorney, Agent, or Firm*—Sheela Mohan-Peterson; Lucy J. Billings; Incyte Pharmaceuticals, Inc.

[57] ABSTRACT

The present invention provides a double-stranded RNA-binding protein (BINDR) and polynucleotides which identify and encode BINDR. The invention also provides expression vectors, host cells, agonists, antibodies, and antagonists. The invention also provides methods for treating disorders associated with expression of BINDR.

8 Claims, 6 Drawing Sheets

```
5' GGG AGT CGG AGG AGG TGG CGG CGC TGG AGC TCC TCC CGG GGA CCA GCG ACC CGG   54
        9        18        27        36        45

GGA GCG AGC ACG TCG CTC CGC ACC GCT CTT CCT CCA GCC GCT GAG CCG TCC CTT   108
       63        72        81        90        99

CTC GCC ATG TCC CAG AGC AGC CAC CGC GCC GAG GCC CCG CCG CTG GAG CGC GAG   162
        M   S   Q   S   S   H   R   A   E   A   P   P   L   E   R   E
       117       126       135       144       153

GAC AGT GGG ACC TTC AGT TTG GGG AAG ATG ATA ACA GCT AAG AAC CCA GGG AAA ACA   216
 D   S   G   T   F   S   L   G   K   M   I   T   A   K   N   P   G   K   T
       171       180       189       198       207

CCG ATT CAG GTA TTA CAC GAA TAC CAG ATG GGC ATG AAG AAC AAG ATC CCA GTT TAT   270
 P   I   Q   V   L   H   E   Y   Q   M   G   M   K   T   K   N   I   P   V   Y
       225       234       243       252       261

GAA TGT GAA AGA TCT GAT GTG CAA ATA CAC GTG CCC ACT TTC ACC TTC AGA GTA   324
 E   C   E   R   S   D   V   Q   I   H   V   P   T   F   T   F   R   V
       279       288       297       306       315

ACC GTT GGT GAC ATA ACC TGC ACA GGT GAA GGT ACA AGT AAG CTG GCG AAA   378
 T   V   G   D   I   T   C   T   G   E   G   T   S   K   L   A   K
       333       342       351       360       369
```

FIGURE 1A

```
     387         396         405         414         423         432
CAT AGA GCT GCA GAG GCT GCC ATA AAC ATT TTG AAA GCC AAT GCA AGT ATT TGC
 H   R   A   A   E   A   A   I   N   I   L   K   A   N   A   S   I   C 441         450         459         468         477         486
TTT GCA GTT CCT GAC CCC TTA ATG CCT GAC CCT TCC AAG CAA CCA AAG AAC CAG
 F   A   V   P   D   P   L   M   P   D   P   S   K   Q   P   K   N   Q 495         504         513         522         531         540
CTT AAT CCT ATT GGT TCA TTA CAG GAA TTG GCT CCT GGA GGA CCT GGC TGG AGA CTT
 L   N   P   I   G   S   L   Q   E   L   A   P   G   G   P   G   W   R   L 549         558         567         576         585         594
CCT GAA TAT ACC CTT ATT CAT CAT AAG GGA CCT GCT CAT AAG AGA GAA TAT ACT
 P   E   Y   T   L   I   H   H   K   G   P   A   H   K   R   E   Y   T 603         612         621         630         639         648
ACA ATT TGC AGG CTA GAG TCA TTT ATG GAA ACT GGA AAG GGG GCA TCA AAA AAG
 T   I   C   R   L   E   S   F   M   E   T   G   K   G   A   S   K   K 657         666         675         684         693         702
CAA GCC AAA AGG AAT GCT GAG TCC TTT CTT GCC AAA TTT AGT AAT ATT TCT
 Q   A   K   R   N   A   E   S   F   L   A   K   F   S   N   I   S 711         720         729         738         747         756
CCA GAG AAC CAC ATT TCT TTA ACA AAT GTA GTA GGA CAT TCT TTA GGA TGT ACT
 P   E   N   H   I   S   L   T   N   V   V   G   H   S   L   G   C   T
```

FIGURE 1B

```
         765         774         783         792         801         810
TGG CAT TCC TTG AGG AAT TCT CCT GGT GAA AAG ATC AAC TTA CTG AAA AGA AGC
 W   H   S   L   R   N   S   P   G   E   K   I   N   L   L   K   R   S 819         828         837         846         855         864
CTC CTT AGT ATT CCA AAT ACA GAT TAC ATC CAG CTG CTT AGT GAA ATT GCC AAG
 L   L   S   I   P   N   T   D   Y   I   Q   L   L   S   E   I   A   K 873         882         891         900         909         918
GAA CAA GGT TTT AAT ATA ACA TAT TTG GAT ATA GAT GAA CTG AGC AGC GCC AAT GGA
 E   Q   G   F   N   I   T   Y   L   D   I   D   E   L   S   S   A   N   G 927         936         945         954         963         972
CAA TAT CAA TGT CTT GCT GAA CTG TCC ACC AGC ATC ACA GTC TGT CAT GGC
 Q   Y   Q   C   L   A   E   L   S   T   S   I   T   V   C   H   G 981         990         999        1008        1017        1026
TCC GGT ATC TCC TGT GGC AAT GCA CAA AGT GAT GCA GCT CAC AAT GCT TTG CAG
 S   G   I   S   C   G   N   A   Q   S   D   A   A   H   N   A   L   Q 1035        1044        1053        1062        1071        1080
TAT TTA AAG ATA ATA GCA GAA AGA AAG TAA ATC TGG AGC AAC TTA AAA AAT CTT
 Y   L   K   I   I   A   E   R   K 1089        1098        1107        1116        1125        1134
TCA GTA GCA CAT AAA AAG TTC CCC TCT GGC CCC TTC CCA AGT AAA ACT TTT ACC
```

FIGURE 1C

```
      1143            1152            1161          1170          1179          1188
GTA GTG TTT ATG TCT TGT TTC TAA ATC TCT TCA TAG ATT CCA TCA ACA CTC CAG 1197            1206            1215          1224          1233          1242
ATT TAA TTA TCT CCT CAT AGT TGT TAT TAA GCT CTT TTT AAT GGC TTC AAC TTT 1251            1260            1269          1278          1287          1296
GTA TCA GTA TAC TGT ATT TAT AAA CTT TGT ACC ACA AGA GAG AGT GTA GCA CCC 1305            1314            1323          1332          1341          1350
ATT TTA CAG TGC CAT GCA CAT CAG AGA AAG AAA CTG CAT GTT TGT TGT TGA TGA 1359            1368            1377          1386          1395          1404
TGA AAT AAA AAT GCT AGC GAC AGT CTT TCT TAC TGG TGC TTA AGC TCT TCT TTG 1413            1422            1431          1440          1449          1458
CAC AAA GCT TTA TAA AGG GAA TTC AAA GGA AGC CCT TTA GAA TTA GAG TCT TGA 1467            1476            1485          1494          1503          1512
GGG ACA GCA CTA ACA GGC CTT TAT TAA GTA TGA TTG ATT GTT AAA TTT CAG GGA 1521            1530            1539          1548          1557          1566
ACA TGA TTG GTC TGC TGT GTA TTT GAA TTC ATG TAA CAA AGA ACT GTT ACG ATG 1575            1584            1593          1602
GGA TTC TGC TCA TTT TAT TAA AAA GCT ACT GAC TTG ACT GTC   3'
```

FIGURE 1D

| | | | |
|---|---|---|---|
| 1 | MSQSRHRAEAPPLEREDSGTFSLGKMITAKPGKTPIQVLH | 620438 |
| 1 | MSSEKPT------------SLNAMRATNPCETPIQLLH | GI 214739 |
| 1 | MSEEQGSGTTT--------GCGLPSIEQMLAANPGKTPISLLQ | GI 478990 |
| 1 | MSEEDQGSGTTT--------GCGLPSIEQMLAANPGKTPISLLQ | GI 1737216 |
| 41 | EYGMKTKNIPVYECERSDVQIHVPTFRVTVGDITCTGE | 620438 |
| 27 | EFGTKTGNHPVYTLEKAEGQAHNPSFTFRLVIGDITSLGE | GI 214739 |
| 37 | EYGTRIGKTPVYDLLKAEGQAHQPNFTFRVTVGDTSCTGQ | GI 478990 |
| 37 | EYGTRIGKTPVYDLLKEEGQAHQPNFTFRVTVGDTSCTGT | GI 1737216 |
| 81 | GTSKKLAKHRAAEAAINILKANA-----SICFAVPDP | 620438 |
| 67 | GPSKKTPKQKAAAEFALNILRGDT-----SKCLPVTDT | GI 214739 |
| 77 | GPSKKAAKHKAAEVALKHLKGGSMLEPALEDSSSESPLDS | GI 478990 |
| 77 | GPSKKAAKHKAAEVALKHLKGGSMLEPALEDSSSLSLLDS | GI 1737216 |
| 113 | LMPD-------------------PSKQPKN- | 620438 |
| 99 | LR-D-------------------PKKPPNQM | GI 214739 |
| 117 | SLPEDDIPVFTAAAAAATPVPSVVLTRSQPPVSPQQS | GI 478990 |
| 117 | SPPEDTPV-VAAAAEAAAPVPSAVLTRSPPMEMQPPVSPQQS | GI 1737216 |
| 124 | QLNPIGSLQELAIHHGWRLPEYTLSQEGGPAHKREYTTIC | 620438 |
| 110 | QENPVGSLQELAVVQKGWRLPEYTVAQESGPPHKREFTITC | GI 214739 |
| 157 | ECNPVGALQELVVSPAHRKEFTMTC | GI 478990 |
| 156 | ECNPVGALQELVVQKGWRLPEYMVTQESGPAHRKEFTMTC | GI 1737216 |

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 313 amino acids
( B ) TYPE: amino acid
( C ) STRANDEDNESS: single
( D ) TOPOLOGY: linear ( v i i ) IMMEDIATE SOURCE:
( A ) LIBRARY: PGANNOT01
( B ) CLONE: 620438

( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Ser | Gln | Ser | Arg | His | Arg | Ala | Glu | Ala | Pro | Pro | Leu | Glu | Arg | Glu |
| 1 | | | | 5 | | | | | 10 | | | | | 15 | |
| Asp | Ser | Gly | Thr | Phe | Ser | Leu | Gly | Lys | Met | Ile | Thr | Ala | Lys | Pro | Gly |
| | | | 20 | | | | | 25 | | | | | 30 | | |
| Lys | Thr | Pro | Ile | Gln | Val | Leu | His | Glu | Tyr | Gly | Met | Lys | Thr | Lys | Asn |
| | | 35 | | | | | 40 | | | | | 45 | | | |
| Ile | Pro | Val | Tyr | Glu | Cys | Glu | Arg | Ser | Asp | Val | Gln | Ile | His | Val | Pro |
| | 50 | | | | | 55 | | | | | 60 | | | | |
| Thr | Phe | Thr | Phe | Arg | Val | Thr | Val | Gly | Asp | Ile | Thr | Cys | Thr | Gly | Glu |
| 65 | | | | | 70 | | | | | 75 | | | | | 80 |
| Gly | Thr | Ser | Lys | Lys | Leu | Ala | Lys | His | Arg | Ala | Ala | Glu | Ala | Ala | Ile |
| | | | | 85 | | | | | 90 | | | | | 95 | |
| Asn | Ile | Leu | Lys | Ala | Asn | Ala | Ser | Ile | Cys | Phe | Ala | Val | Pro | Asp | Pro |
| | | | 100 | | | | | 105 | | | | | 110 | | |
| Leu | Met | Pro | Asp | Pro | Ser | Lys | Gln | Pro | Lys | Asn | Gln | Leu | Asn | Pro | Ile |
| | | 115 | | | | | 120 | | | | | 125 | | | |

```
Gly Ser Leu Gln Glu Leu Ala Ile His His Gly Trp Arg Leu Pro Glu
    130                 135                 140
Tyr Thr Leu Ser Gln Glu Gly Gly Pro Ala His Lys Arg Glu Tyr Thr
145                     150                 155                 160
Thr Ile Cys Arg Leu Glu Ser Phe Met Glu Thr Gly Lys Gly Ala Ser
                165                 170                 175
Lys Lys Gln Ala Lys Arg Asn Ala Ala Glu Lys Phe Leu Ala Lys Phe
            180                 185                 190
Ser Asn Ile Ser Pro Glu Asn His Ile Ser Leu Thr Asn Val Val Gly
            195                 200                 205
His Ser Leu Gly Cys Thr Trp His Ser Leu Arg Asn Ser Pro Gly Glu
    210                 215                 220
Lys Ile Asn Leu Leu Lys Arg Ser Leu Leu Ser Ile Pro Asn Thr Asp
225                 230                 235                 240
Tyr Ile Gln Leu Leu Ser Glu Ile Ala Lys Glu Gln Gly Phe Asn Ile
                245                 250                 255
Thr Tyr Leu Asp Ile Asp Glu Leu Ser Ala Asn Gly Gln Tyr Gln Cys
            260                 265                 270
Leu Ala Glu Leu Ser Thr Ser Pro Ile Thr Val Cys His Gly Ser Gly
    275                 280                 285
Ile Ser Cys Gly Asn Ala Gln Ser Asp Ala Ala His Asn Ala Leu Gln
    290                 295                 300
Tyr Leu Lys Ile Ile Ala Glu Arg Lys
305                 310
```

(2) INFORMATION FOR SEQ ID NO:2:

(i) SEQUENCE CHARACTERISTICS:
        (A) LENGTH: 1608 base pairs
        (B) TYPE: nucleic acid
        (C) STRANDEDNESS: single
        (D) TOPOLOGY: linear (vii) IMMEDIATE SOURCE:
        (A) LIBRARY: PGANNOT01
        (B) CLONE: 620438

(xi) SEQUENCE DESCRIPTION: SEQ ID NO:2:

```
GGGAGTCGGA GGAGGTGGCG GCGCTGGAGC TCCTCCCGGG GACCAGCGAC CCGGGGAGCG      60
AGCACGTCGC TCCGCACCGC TCTTCCTCCA GCCGCTGAGC CGTCCCTTCT CGCCATGTCC     120
CAGAGCAGGC ACCGCGCCGA GGCCCCGCCG CTGGAGCGCG AGGACAGTGG GACCTTCAGT     180
TTGGGGAAGA TGATAACAGC TAAGCCAGGG AAAACACCGA TTCAGGTATT ACACGAATAC     240
GGCATGAAGA CCAAGAACAT CCCAGTTTAT GAATGTGAAA GATCTGATGT GCAAATACAC     300
GTGCCCACTT TCACCTTCAG AGTAACCGTT GGTGACATAA CCTGCACAGG TGAAGGTACA     360
AGTAAGAAGC TGGCGAAACA TAGAGCTGCA GAGGCTGCCA TAAACATTTT GAAAGCCAAT     420
GCAAGTATTT GCTTTGCAGT TCCTGACCCC TTAATGCCTG ACCCTTCCAA GCAACCAAAG     480
AACCAGCTTA ATCCTATTGG TTCATTACAG GAATTGGCTA TTCATCATGG CTGGAGACTT     540
CCTGAATATA CCCTTTCCCA GGAGGGAGGA CCTGCTCATA AGAGAGAATA TACTACAATT     600
TGCAGGCTAG AGTCATTTAT GGAAACTGGA AAGGGGCAT CAAAAAAGCA AGCCAAAAGG      660
AATGCTGCTG AGAAATTTCT TGCCAAATTT AGTAATATTT CTCCAGAGAA CCACATTTCT     720
TTAACAAATG TAGTAGGACA TTCTTTAGGA TGTACTTGGC ATTCCTTGAG GAATTCTCCT     780
GGTGAAAAGA TCAACTTACT GAAAAGAAGC CTCCTTAGTA TTCCAAATAC AGATTACATC     840
```

-continued

```
CAGCTGCTTA GTGAAATTGC CAAGGAACAA GGTTTTAATA TAACATATTT GGATATAGAT      900

GAACTGAGCG CCAATGGACA ATATCAATGT CTTGCTGAAC TGTCCACCAG CCCCATCACA      960

GTCTGTCATG GCTCCGGTAT CTCCTGTGGC AATGCACAAA GTGATGCAGC TCACAATGCT     1020

TTGCAGTATT TAAAGATAAT AGCAGAAAGA AAGTAAATCT GGAGCAACTT AAAAAATCTT     1080

TCAGTAGCAC ATAAAAAGTT CCCCTCTGGC CCCTTCCAA GTAAAACTTT TACCGTAGTG      1140

TTTATGTCTT GTTTCTAAAT CTCTTCATAG ATTCCATCAA CACTCCAGAT TTAATTATCT     1200

CCTCATAGTT GTTATTAAGC TCTTTTTAAT GGCTTCAACT TTGTATCAGT ATACTGTATT     1260

TATAAACTTT GTACCACAAG AGAGAGTGTA GCACCCATTT TACAGTGCCA TGCACATCAG     1320

AGAAAGAAAC TGCATGTTTG TTGTTGATGA TGAAATAAAA ATGCTAGCGA CAGTCTTTCT     1380

TACTGGTGCT TAAGCTCTTC TTTGCACAAA GCTTTATAAA GGGAATTCAA AGGAAGCCCT     1440

TTAGAATTAG AGTCTTGAGG GACAGCACTA ACAGGCCTTT ATTAAGTATG ATTGATTGTT     1500

AAATTTCAGG GAACATGATT GGTCTGCTGT GTATTTGAAT TCATGTAACA AAGAACTGTT     1560

ACGATGGGAT TCTGCTCATT TTATTAAAAA GCTACTGACT TGACTGTC                  1608
```

( 2 ) INFORMATION FOR SEQ ID NO:3:

( i ) SEQUENCE CHARACTERISTICS:
        ( A ) LENGTH: 298 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 214739

( x i ) SEQUENCE DESCRIPTION: SEQ ID NO:3:

```
Met Ser Ser Glu Lys Pro Thr Ser Leu Asn Ala Met Arg Ala Thr Asn
 1               5                  10                  15

Pro Cys Glu Thr Pro Ile Gln Leu Leu His Glu Phe Gly Thr Lys Thr
                20                  25                  30

Gly Asn His Pro Val Tyr Thr Leu Glu Lys Ala Glu Gly Gln Ala His
            35                  40                  45

Asn Pro Ser Phe Thr Phe Arg Leu Val Ile Gly Asp Ile Thr Ser Leu
        50                  55                  60

Gly Glu Gly Pro Ser Lys Lys Thr Pro Lys Gln Lys Ala Ala Glu Phe
65                  70                  75                  80

Ala Leu Asn Ile Leu Arg Gly Asp Thr Ser Lys Cys Leu Pro Val Thr
                85                  90                  95

Asp Thr Leu Arg Asp Pro Lys Lys Pro Asn Gln Met Gln Glu Asn
                100                 105                 110

Pro Val Gly Ser Leu Gln Glu Leu Ala Val Gln Lys Gly Trp Arg Leu
            115                 120                 125

Pro Glu Tyr Thr Val Ala Gln Glu Ser Gly Pro Pro His Lys Arg Glu
        130                 135                 140

Phe Thr Ile Thr Cys Arg Val Glu Thr Phe Val Glu Thr Gly Ser Gly
145                 150                 155                 160

Thr Ser Lys Gln Val Ala Lys Arg Val Ala Ala Glu Lys Leu Leu Thr
                165                 170                 175

Lys Phe Lys Thr Ile Ser Thr Asp Asn Ile Pro Leu Asn Lys Leu Ile
                180                 185                 190

Gly Asn Lys Met Gly Cys Thr Trp Asp Ser Met Arg Asn Ser Ser Gly
            195                 200                 205
```

```
Glu  Lys  Ile  Ser  Met  Leu  Lys  Arg  Ser  Pro  Leu  Ser  Ile  Pro  Asn  Thr
     210                      215                      220

Asp  Tyr  Val  Lys  Met  Leu  Lys  Asp  Val  Ala  Glu  Glu  Leu  Asp  Phe  Asn
225                           230                      235                      240

Leu  Thr  Tyr  Leu  Asp  Ile  Asp  Glu  Leu  Ser  Val  Asn  Gly  Gln  Tyr  Gln
                    245                      250                      255

Cys  Leu  Ala  Glu  Leu  Ser  Thr  Asn  Pro  Ile  Thr  Val  Cys  His  Gly  Thr
               260                      265                      270

Gly  Ile  Ser  Cys  Gly  Asn  Ala  His  Asn  Asp  Ala  Ala  His  Asn  Ala  Leu
          275                      280                      285

Gln  Tyr  Leu  Lys  Ile  Met  Cys  Ile  Lys  Lys
     290                      295
```

( 2 ) INFORMATION FOR SEQ ID NO:4:

( i ) SEQUENCE CHARACTERISTICS:
        ( A ) LENGTH: 366 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 478990

( x i ) SEQUENCE DESCRIPTION: SEQ ID NO:4:

```
Met  Ser  Glu  Glu  Glu  Gln  Gly  Ser  Gly  Thr  Thr  Thr  Gly  Cys  Gly  Leu
1                        5                        10                       15

Pro  Ser  Ile  Glu  Gln  Met  Leu  Ala  Ala  Asn  Pro  Gly  Lys  Thr  Pro  Ile
               20                       25                       30

Ser  Leu  Leu  Gln  Glu  Tyr  Gly  Thr  Arg  Ile  Gly  Lys  Thr  Pro  Val  Tyr
          35                       40                       45

Asp  Leu  Leu  Lys  Ala  Glu  Gly  Gln  Ala  His  Gln  Pro  Asn  Phe  Thr  Phe
     50                       55                       60

Arg  Val  Thr  Val  Gly  Asp  Thr  Ser  Cys  Thr  Gly  Gln  Gly  Pro  Ser  Lys
65                       70                       75                       80

Lys  Ala  Ala  Lys  His  Lys  Ala  Ala  Glu  Val  Ala  Leu  Lys  His  Leu  Lys
               85                       90                       95

Gly  Gly  Ser  Met  Leu  Glu  Pro  Ala  Leu  Glu  Asp  Ser  Ser  Ser  Phe  Ser
               100                      105                      110

Pro  Leu  Asp  Ser  Ser  Leu  Pro  Glu  Asp  Ile  Pro  Val  Phe  Thr  Ala  Ala
          115                      120                      125

Ala  Ala  Ala  Thr  Pro  Val  Pro  Ser  Val  Val  Leu  Thr  Arg  Ser  Pro  Ala
     130                      135                      140

Met  Glu  Leu  Gln  Pro  Pro  Val  Ser  Pro  Gln  Gln  Ser  Glu  Cys  Asn  Pro
145                      150                      155                      160

Val  Gly  Ala  Leu  Gln  Glu  Leu  Val  Val  Gln  Lys  Gly  Trp  Arg  Leu  Pro
               165                      170                      175

Glu  Tyr  Thr  Val  Thr  Gln  Glu  Ser  Gly  Pro  Ala  His  Arg  Lys  Glu  Phe
          180                      185                      190

Thr  Met  Thr  Cys  Arg  Val  Glu  Arg  Phe  Ile  Glu  Ile  Gly  Ser  Gly  Thr
     195                      200                      205

Ser  Lys  Lys  Leu  Ala  Lys  Arg  Asn  Ala  Ala  Ala  Lys  Met  Leu  Leu  Arg
     210                      215                      220

Val  His  Thr  Val  Pro  Leu  Asp  Ala  Arg  Asp  Gly  Asn  Glu  Val  Glu  Pro
225                      230                      235                      240

Asp  Asp  Asp  His  Phe  Ser  Ile  Gly  Val  Gly  Phe  Arg  Leu  Asp  Gly  Leu
                    245                      250                      255
```

Arg Asn Arg Gly Pro Gly Cys Thr Trp Asp Ser Leu Arg Asn Ser Val
                260                 265                 270

Gly Glu Lys Ile Leu Ser Leu Arg Ser Cys Ser Leu Gly Ser Leu Gly
            275                 280                 285

Ala Leu Gly Pro Ala Cys Cys Arg Val Leu Ser Glu Leu Ser Glu Glu
            290                 295                 300

Gln Ala Phe His Val Ser Tyr Leu Asp Ile Glu Glu Leu Ser Leu Ser
305                     310                 315                 320

Gly Leu Cys Gln Cys Leu Val Glu Leu Ser Thr Gln Pro Ala Thr Val
                325                 330                 335

Cys His Gly Ser Ala Thr Thr Arg Glu Ala Ala Arg Gly Glu Ala Ala
            340                 345                 350

Arg Arg Ala Leu Gln Tyr Leu Lys Ile Met Ala Gly Ser Lys
            355                 360                 365

(2) INFORMATION FOR SEQ ID NO:5:

(i) SEQUENCE CHARACTERISTICS:
        (A) LENGTH: 365 amino acids
        (B) TYPE: amino acid
        (C) STRANDEDNESS: single
        (D) TOPOLOGY: linear (xi) SEQUENCE DESCRIPTION: SEQ ID NO:5:

Met Ser Glu Glu Asp Gln Gly Ser Gly Thr Thr Gly Cys Gly Leu
1               5                   10                  15

Pro Ser Ile Glu Gln Met Leu Ala Ala Asn Pro Gly Lys Thr Pro Ile
                20                  25                  30

Ser Leu Leu Gln Glu Tyr Gly Thr Arg Ile Gly Lys Thr Pro Val Tyr
            35                  40                  45

Asp Leu Leu Lys Glu Glu Gly Gln Ala His Gln Pro Asn Phe Thr Phe
    50                  55                  60

Arg Val Thr Val Gly Asp Thr Ser Cys Thr Gly Thr Gly Pro Ser Lys
65                  70                  75                  80

Lys Ala Ala Lys His Lys Ala Ala Glu Val Ala Leu Lys His Leu Lys
                85                  90                  95

Gly Gly Ser Met Leu Glu Pro Ala Leu Glu Asp Ser Ser Leu Ser
            100                 105                 110

Leu Leu Asp Ser Ser Pro Pro Glu Asp Thr Pro Val Val Ala Ala Glu
        115                 120                 125

Ala Ala Ala Pro Val Pro Ser Ala Val Leu Thr Arg Ser Pro Pro Met
    130                 135                 140

Glu Met Gln Pro Pro Val Ser Pro Gln Gln Ser Glu Cys Asn Pro Val
145                 150                 155                 160

Gly Ala Leu Gln Glu Leu Val Val Gln Lys Gly Trp Arg Leu Pro Glu
                165                 170                 175

Tyr Met Val Thr Gln Glu Ser Gly Pro Ala His Arg Lys Glu Phe Thr
            180                 185                 190

Met Thr Cys Arg Val Glu Arg Phe Ile Glu Ile Gly Ser Gly Thr Ser
        195                 200                 205

Lys Lys Leu Ala Lys Arg Asn Ala Ala Ala Lys Met Leu Leu Arg Val
    210                 215                 220

His Thr Val Pro Leu Asp Ala Arg Asp Gly Asn Glu Ala Glu Pro Asp
225                 230                 235                 240

Asp Asp His Phe Ser Ile Gly Val Ser Ser Arg Leu Asp Gly Leu Arg
                245                 250                 255

| | | | | | | | | | | | | | | | |
|---|---|---|---|---|---|---|---|---|---|---|---|---|---|---|---|
| Asn | His | Gly | Pro 260 | Gly | Cys | Thr | Trp | Asp 265 | Ser | Leu | Arg | Asn | Ser 270 | Val | Gly |
| Glu | Lys | Ile 275 | Leu | Ser | Leu | Arg | Ser 280 | Cys | Ser | Val | Gly | Ser 285 | Leu | Gly | Ala |
| Leu | Gly 290 | Ser | Ala | Cys | Cys | Ser 295 | Val | Leu | Ser | Glu | Leu 300 | Ser | Glu | Glu | Gln |
| Ala 305 | Phe | His | Val | Ser | Tyr 310 | Leu | Asp | Ile | Glu | Gln 315 | Leu | Ser | Leu | Ser | Gly 320 |
| Leu | Cys | Gln | Cys | Leu 325 | Val | Glu | Leu | Ser | Thr 330 | Gln | Pro | Ala | Ala | Val 335 | Cys |
| Tyr | Gly | Ser | Ala 340 | Thr | Thr | Arg | Glu | Ala 345 | Ala | Arg | Gly | Asp | Ala 350 | Ala | His |
| Arg | Ala | Leu 355 | Gln | Tyr | Leu | Arg | Ile 360 | Met | Ala | Gly | Ser | Lys 365 | | | |

DOUBLE-STRANDED RNA-BINDING PROTEIN

FIELD OF THE INVENTION

This invention relates to nucleic acid and amino acid sequences of a double-stranded RNA-binding protein and to the use of these sequences in the diagnosis, prevention, and treatment of disorders associated with cancer and disorders of cellular growth.

BACKGROUND OF THE INVENTION

RNA-binding proteins are essential for a wide variety of cellular and developmental functions. They participate in RNA processing, editing, transport, localization, stabilization, and the posttranscriptional control of mRNAs. The RNA binding activity of these proteins is mediated by specific RNA-binding domains contained within the proteins. A variety of conserved RNA binding motifs have been defined through comparisons of amino acid homologies and structural similarities within these RNA-binding domains. These motifs include the RNP motif, an arginine-rich motif, the zinc-finger motif, the Y-box, the KH motif, and the double-stranded RNA-binding domain (dsRBD), all of which are characterized by specific consensus sequences (Burd, C. G. and Dreyfuss, G. (1994) Science 265:615–621).

The double-stranded RNA-binding domain (dsRBD) exclusively binds double-stranded RNA or RNA-DNA. A dsRBD motif consists of a region of approximately 70 amino acids which includes basic residues and contains a conserved core sequence with a predicted α-helical structure. The dsRBD motif is found in at least 20 known or putative RNA-binding proteins from different organisms. There are two types of dsRBDs; Type A, which is homologous along its entire length with the defined consensus sequence, and Type B, which is more highly conserved at its C terminus than its N terminus. These domains have been functionally delineated in specific proteins by deletion analysis and RNA binding assays (St Johnston, D., et al. (1992) Proc. Natl. Acad. Sci. 89:10979–10983).

Double stranded RNA-binding proteins participate in posttranscriptional regulation pathways which control gene expression. Posttranscriptional regulation allows the modulation of protein expression in the absence of new transcription and is active during entry into the M phase of the cell cycle, in viral infections, and in stress and heat shock conditions. The human cellular TAR RNA binding proteins (TRBP and TRBP2), contain two dsRBDs and participate in the trans-activation of human immunodeficiency virus type-1 (HIV-1) genes. On integration into the host genome, HIV-1 remains latent until basal transcription produces a threshold level of the viral trans-activator protein, Tat. Tat increases the rate of viral mRNA production by increasing the elongation capacity of RNA polymerase. Tat interacts with the transcription machinery after binding to the trans-activation-responsive (TAR) RNA stem-loop element found at the 5 end of all HIV-1 transcripts. TRBP and TRBP2 proteins bind to TAR RNA with TAT and synergistically effect trans-activation. Biologically, TRBP has a growth-promoter effect and when overexpressed produces a transformed cell phenotype (Gatignol, A., et al. (1996) Gene Expression 5:217–228).

Gene expression is also down-regulated by dsRBDs, as has been shown with the mammalian double-stranded RNA-dependent protein kinase (PAR). PAR, which is a cell growth inhibitor, is activated by binding to double-stranded RNA or to single-stranded RNA with double-stranded regions (viral RNA or cellular RNA stem-loop structures). Activated PKR phosphorylates eukaryotic initiation factor eIF-2a inhibiting translation and preventing viral replication. The mouse Prbp protein, which contains two dsRBDs, affects the level of the Prm-1 gene by repressing its transcription and allowing normal spermatid differentiation (Benkirane, M. et al. (1997) EMBO J. 16: 611–624; Lee, K. et al. (1999) Mol. Cell. Biol. 16:3023–3034).

The discovery of a double-stranded RNA-binding protein and the polynucleotides encoding it satisfies a need in the art by providing new compositions which are useful in the diagnosis, prevention and treatment of cancer and disorders of cell growth.

SUMMARY OF THE INVENTION

The present invention features a double-stranded RNA-binding protein hereinafter designated BINDR and characterized as having similarity to *Xenopus laevis* Xlrbpa-1, human TRBP2, and mouse Prbp.

Accordingly, the invention features a substantially purified double-stranded RNA-binding protein having the amino acid sequence shown in SEQ ID NO:1.

One aspect of the invention features isolated and substantially purified polynucleotides that encode BINDR. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features fragments or portions of the polynucleotides that encode BINDR. The present invention also features antibodies which bind specifically to BINDR, and pharmaceutical compositions comprising substantially purified BINDR. The invention also features agonists and antagonists of BINDR. The invention also features a method for treating disorders associated with decreased BINDR by administering BINDR and a method for treating disorders associated with increased BINDR by administering an antagonist to BINDR.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of BINDR. The alignment was produced using MACDNA-SIS PRO™ software (Hitachi Software Engineering Co., Ltd., San Bruno, Calif.).

Figure 2B:
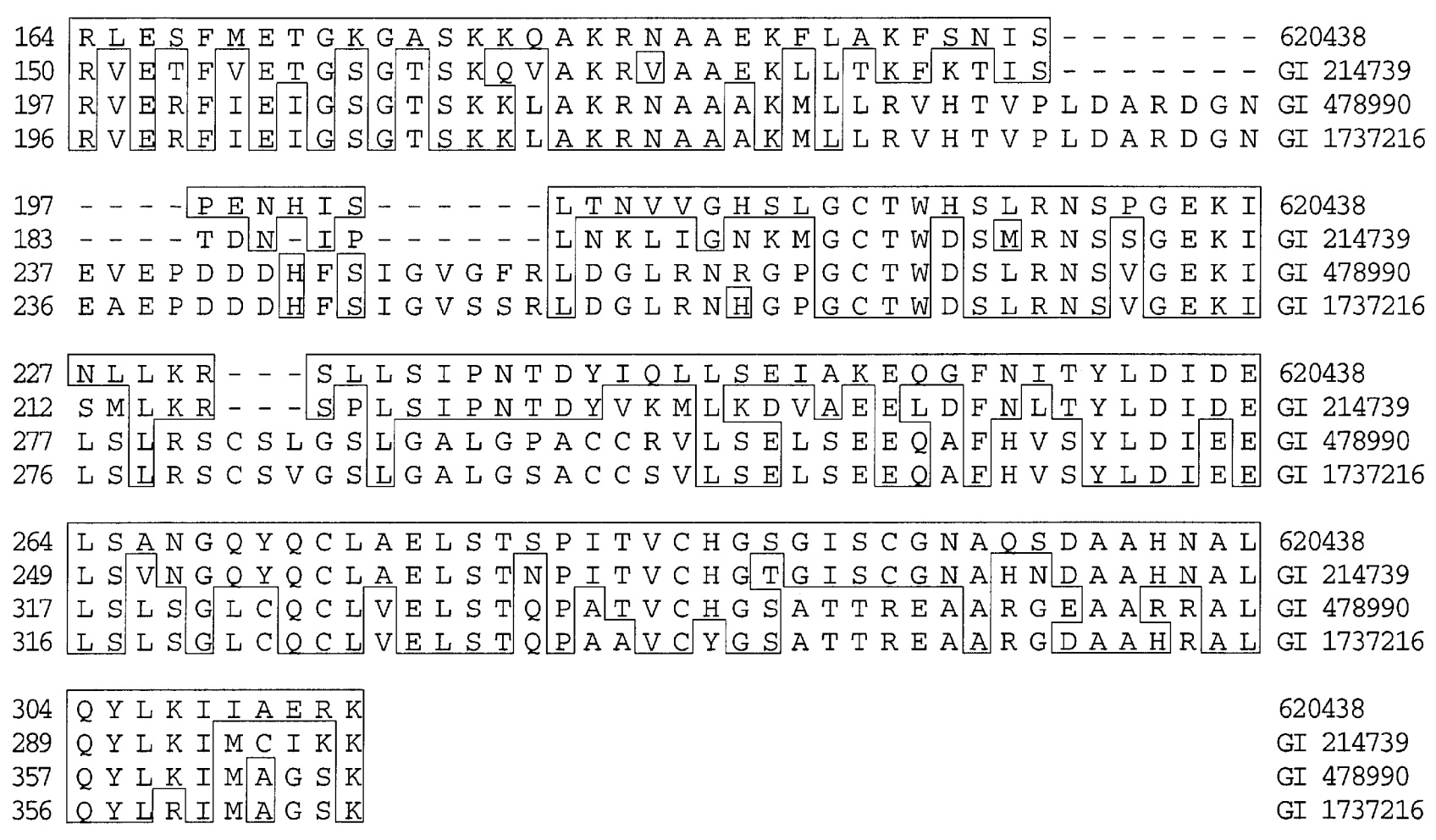

FIGS. 2A and 2B show the amino acid sequence alignments among BINDR (SEQ ID NO:1), *Xenopus laevis* Xlrbpa-1 (GI 214739, SEQ ID NO:3), human TRBP2 (GI 478990, SEQ ID NO:5), and mouse Prbp (GI 1737216, SEQ ID NO:7). The alignment was produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that, as used herein, and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

BINDR, as used herein, refers to the amino acid sequences of substantially purified BINDR obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW Fragment Assembly system (GCG, Madison, Wis.), or which has been both extended and assembled.

A "variant" of BINDR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic BINDR, or any oligopeptide thereof, to induce a specific immune response in appropriate animals or cells and to bind with specific antibodies.

The term "agonist", as used herein, refers to a molecule which, when bound to BINDR, causes a change in BINDR which modulates the activity of BINDR. Agonists may include proteins, nucleic acids, carbohydrates, or any other molecules which bind to BINDR.

The terms "antagonist" or "inhibitor", as used herein, refer to a molecule which, when bound to BINDR, blocks or modulates the biological or immunological activity of BINDR. Antagonists and inhibitors may include proteins, nucleic acids, carbohydrates, or any other molecules which bind to BINDR.

The term "modulate", as used herein, refers to a change or an alteration in the biological activity of BINDR. Modulation may be an increase or a decrease in protein activity, a change in binding characteristics, or any other change in the biological, functional or immunological properties of BINDR.

The term "mimetic", as used herein, refers to a molecule, the structure of which is developed from knowledge of the structure of BINDR or portions thereof and, as such, is able to effect some or all of the actions of BINDR-like molecules.

The term "derivative", as used herein, refers to the chemical modification of a nucleic acid encoding BINDR or the encoded BINDR. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm $-5°$ C. ($5°$ C. below the melting temperature (Tm) of the probe) to about $20°$ C. to $25°$ C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human BINDR and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunooen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding BINDR or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding BINDR in a sample and thereby correlates with expression of the transcript from the polynucleotide encoding the protein.

"Alterations" in the polynucleotide of SEQ ID NO:2, as used herein, comprise any alteration in the sequence of polynucleotides encoding BINDR including deletions, insertions, and point mutations that may be detected using hybridization assays. Included within this definition is the detection of alterations to the genomic DNA sequence which encodes BINDR (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding BINDR (e.g., using fluorescent in situ hybridization [FISH] to metaphase chromosome spreads).

As used herein, the term "antibody" refers to intact molecules as well as fragments thereof, such as Fa, F(ab')$_2$, and Fv, which are capable of binding the epitopic determinant. Antibodies that bind BINDR polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a double-stranded RNA-binding protein, (BINDR), the polynucleotides encoding BINDR, and the use of these compositions for the diagnosis, prevention, or treatment of disorders associated with increased or decreased expression of BINDR including cancer, inflammatory disorders, and viral infections.

Nucleic acids encoding the human BINDR of the present invention were first identified in Incyte Clone 620438 from the paraganglion cDNA library, PGANNOT01, through a computer search for amino acid sequence alignments. The complete nucleotide sequence, SEQ ID NO:2, was derived from extension and assembly of Incyte clones 620438 (PGANNOT01), 1253094 (LUNGFET03), 663899 (SCORNOT01), and 1700864, 1701065 (BLADTUT05).

In one embodiment, the invention encompasses a polypeptide comprising the amino acid sequence of SEQ ID NO:1, as shown in FIGS. 1A, 1B, 1C and 1D. BINDR is 313 amino acids in length and has chemical and structural homology with Xlrbpa-1 (SEQ ID NO:3), TRBP2 (SEQ ID NO:5), and Prbp (SEQ ID NO:7). In particular, BINDR shares 59% identity with Xlrbpa-1, and 47% identity with both TRBP2 and Prbp. BINDR contains two double-stranded RNA-binding domain core sequence motifs, in the regions from G79 to L99 and from G172 to L189, and two potential N-glycosylation sites, at $N_{102}$ and $N_{255}$. Northern analysis shows the expression of BINDR sequence in various libraries, a majority of which are associated with cancers, transformed cells, and proliferating tissues.

The invention also encompasses BINDR variants which retain the biological or other functional activity of BINDR. A preferred BINDR variant is one having at least 80%, and more preferably 90%, amino acid sequence identity to the BINDR amino acid sequence (SEQ ID NO:1). A most preferred BINDR variant is one having at least 95% amino acid sequence identity to SEQ ID NO:1.

The invention also encompasses polynucleotides which encode BINDR. Accordingly, any nucleic acid sequence which encodes the amino acid sequence of BINDR can be used to generate recombinant molecules which express BINDR. In a particular embodiment, the invention encompasses the polynucleotide comprising the nucleic acid sequence of SEQ ID NO:2 as shown in FIGS. 1A, 1B, 1C and 1D.

It will be appreciated by those skilled in the art that as a result of the degeneracy of the genetic code, a multitude of nucleotide sequences encoding BINDR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring BINDR, and all such variations are to be considered as being specifically disclosed.

Although nucleotide sequences which encode BINDR and its variants are preferably capable of hybridizing to the nucleotide sequence of the naturally occurring BINDR under appropriately selected conditions of stringency, it may be advantageous to produce nucleotide sequences encoding BINDR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding BINDR and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode BINDR and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding BINDR or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding BINDR which are encompassed by the invention include deletions, insertions, or substitutions of different nucleotides resulting in a polynucleotide that encodes the same or a functionally equivalent BINDR. The encoded protein may also contain deletions, insertions, or substitutions of amino acid residues which produce a silent change and result in a functionally equivalent BINDR. Deliberate amino acid substitutions may be made on the basis of similarity in polarity, charge, solubility, hydrophobicity, hydrophilicity, and/or the amphipathic nature of the residues as long as the biological activity of BINDR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding BINDR. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T 7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding BINDR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode BINDR, or fusion proteins or functional equivalents thereof, may be used in recombinant DNA molecules to direct expression of BINDR in appropriate host cells. Due to the inherent degeneracy of the genetic code, other DNA sequences which encode substantially the same or a functionally equivalent amino acid sequence may be produced and these sequences may be used to clone and express BINDR.

As will be understood by those of skill in the art, it may be advantageous to produce BINDR-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter BINDR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding BINDR may be ligated to a heterologous sequence to encode a fusion protein. For example, to screen peptide libraries for inhibitors of BINDR activity, it may be useful to encode a chimeric BINDR protein that can be recognized by a commercially available antibody. A fusion protein may also be engineered to contain a cleavage site located between the BINDR encoding sequence and the heterologous protein sequence, so that BINDR may be cleaved and purified away from the heterologous moiety.

In another embodiment, sequences encoding BINDR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of BINDR, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of BINDR, or any part thereof, may be altered during direct synthesis and/or combined using chemical methods with sequences from other proteins, or any part thereof, to produce a variant polypeptide.

In order to express a biologically active BINDR, the nucleotide sequences encoding BINDR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding BINDR and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding BINDR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding BINDR, vectors based on SV40 or EBV may be used with an appropriate selectable marker.

In bacterial systems, a number of expression vectors may be selected depending upon the use intended for BINDR. For example, when large quantities of BINDR are needed for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding BINDR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding BINDR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al.

(1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express BINDR. For example, in one such system, *Autographa californica* nuclear polyhedrosis virus (AcNPV) is used as a vector to express foreign genes in *Spodoptera frugiperda* cells or in Trichoplusia larvae. The sequences encoding BINDR may be cloned into a non-essential region of the virus, such as the polyhedrin gene, and placed under control of the polyhedrin promoter. Successful insertion of BINDR will render the polyhedrin gene inactive and produce recombinant virus lacking coat protein. The recombinant viruses may then be used to infect, for example, *S. frugiperda* cells or Trichoplusia larvae in which BINDR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding BINDR may be ligated into an adenovirus transcription/translation complex consisting of the late promoter and tripartite leader sequence. Insertion in a non-essential E1 or E3 region of the viral genome may be used to obtain a viable virus which is capable of expressing BINDR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding BINDR. Such signals include the ATG initiation codon and adjacent sequences. In cases where sequences encoding BINDR, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express BINDR may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding BINDR is inserted within a marker gene sequence, recombinant cells containing sequences encoding BINDR can be identified by the absence of marker gene function. Alternatively, a marker gene can be placed in tandem with a sequence encoding BINDR under the control of a single promoter. Expression of the marker gene in response to induction or selection usually indicates expression of the tandem gene as well.

Alternatively, host cells which contain the nucleic acid sequence encoding BINDR and express BINDR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding BINDR can be detected by DNA-DNA or DNA-RNA hybridization or amplification using probes or portions or fragments of polynucleotides encoding BINDR. Nucleic acid amplification based assays involve the use of oligonucleotides or oligomers based on the sequences encoding BINDR to detect transformants containing DNA or RNA encoding BINDR. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of BINDR, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on BINDR is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding BINDR include oligolabeling, nick translation, end-labeling or PCR amplification using a labeled nucleotide. Alternatively, the sequences encoding BINDR, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding BINDR may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode BINDR may be designed to contain signal sequences which direct secretion of BINDR through a prokaryotic or eukaryotic cell membrane. Other recombinant constructions may be used to join sequences encoding BINDR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and BINDR may be used to facilitate purification. One such expression vector provides for expression of a fusion protein containing BINDR and a nucleic acid encoding 6 histidine residues preceding a thioredoxin or an enterokinase cleavage site.

The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying BINDR from the fusion protein. A discussion of vectors which contain fusion proteins is provided in Kroll, D. J. et al. (1993; DNA Cell Biol. 12:441–453).

In addition to recombinant production, fragments of BINDR may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of BINDR may be chemically synthesized separately and combined using chemical methods to produce the full length molecule.

THERAPEUTICS

Based on the chemical and structural homology between BINDR (SEQ ID NO:1), Xlrbpa-1 (SEQ ID NO:3), TRBP2 (SEQ ID NO:4), and Prbp (SEQ ID NO:5), BINDR is a double-stranded RNA-binding protein which may play a role in posttranslational regulation of gene expression. Proteins with double-stranded RNA-binding domains are able to bind to RNA-DNA duplexes and to RNA stem-loop structures, which are found in both normal and virus infected cells. Proteins which bind double-stranded RNA can either regulate gene expression by acting on a specific gene transcript, or can regulate the expression of a variety of genes by modulating the expression of key proteins within a cellular pathway. In Northern analysis, BINDR sequences are associated with cancerous and proliferating cells and tissues, and as such, may play a role in regulating cell growth.

Therefore, in one embodiment, antagonists or inhibitors of BINDR may be administered to a subject to treat or prevent cancer. These cancers include, but are not limited to, adenocarcinoma, leukemia, lymphoma, melanoma, myeloma, sarcoma, and teratocarcinoma and particularly cancers of the adrenal gland, bladder, bone, brain, breast, cervix, gall bladder, gastrointestinal tract, heart, kidney, liver, lung, ovaries, pancreas, paragangliomas, parathyroid, pituitary gland, prostate, salivary gland, spleen, stomach, thymus, thyroid, testes, and uterus.

In another embodiment, a vector expressing the complement or antisense of the polynucleotide encoding BINDR may be administered to a subject to treat or prevent the cancers listed above. In one aspect, antibodies which are specific for BINDR may be used directly as an antagonist, or indirectly as a targeting or delivery mechanism for bringing a pharmaceutical agent to cells or tissue which express BINDR.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of BINDR may be produced using methods which are generally known in the art. In particular, purified BINDR may be used to produce antibodies or to screen libraries of pharmaceutical agents to identify those which specifically bind BINDR.

Antibodies to BINDR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with BINDR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to BINDR have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of BINDR amino acids may be fused with those of another protein such as keyhole limpet hemocyanin and antibody produced against the chimeric molecule.

Monoclonal antibodies to BINDR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce BINDR-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for BINDR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between BINDR and its specific antibody. A two-site, monoclonal-based immunoassay utilizing monoclonal antibodies reactive to two non-interfering BINDR epitopes is preferred, but a competitive binding assay may also be employed (Maddox, supra).

In another embodiment of the invention, the polynucleotides encoding BINDR, or any fragment thereof, or antisense molecules, may be used for therapeutic purposes. In one aspect, antisense to the polynucleotide encoding BINDR may be used in situations in which it would be desirable to block the transcription of the mRNA. In particular, cells may be transformed with sequences complementary to polynucleotides encoding BINDR. Thus, antisense molecules may be used to modulate BINDR activity, or to achieve regulation of gene function. Such technology is now well known in the art, and sense or antisense oligomers or larger fragments, can be designed from various locations along the coding or control regions of sequences encoding BINDR.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding BINDR. These techniques are described both in Sambrook et al. (supra) and in Ausubel et al. (supra).

Genes encoding BINDR can be turned off by transforming a cell or tissue with expression vectors which express high levels of a polynucleotide or fragment thereof which encodes BINDR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding BINDR, i.e. the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding BINDR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding BINDR. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of BINDR, antibodies to BINDR, mimetics, agonists, antagonists, or inhibitors of BINDR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of BINDR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example BINDR or fragments thereof, antibodies of BINDR, agonists, antagonists or inhibitors of BINDR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind BINDR may be used for the diagnosis of conditions or diseases characterized by expression of BINDR, or in assays to monitor patients being treated with BINDR, agonists, antagonists or inhibitors. The antibodies useful for diagnostic purposes may be prepared in the same manner as those described above for therapeutics. Diagnostic assays for BINDR include methods which utilize the antibody and a label to detect BINDR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring BINDR are known in the art and provide a basis for diagnosing altered or abnormal levels of BINDR expression. Normal or standard values for BINDR expression are established by combining body fluids or cell extracts taken from normal mammalian subjects, preferably human, with antibody to BINDR under conditions suitable for complex formation. The amount of standard complex formation may be quantified by various methods, but preferably by photometric, means. Quantities of BINDR expressed in subject samples, control and disease, biopsied tissues are compared with the standard values. Deviation between standard and subject values establishes the parameters for diagnosing disease.

In another embodiment of the invention, the polynucleotides encoding BINDR may be used for diagnostic purposes. The polynucleotides which may be used include oligonucleotide sequences, complementary or antisense RNA and DNA sequences, and PNAs. The polynucleotides may be used to detect and quantitate gene expression in biopsied tissues in which expression of BINDR may be correlated with disease. The diagnostic assay may be used to distinguish between absence, presence, and excess expression of BINDR, and to monitor regulation of BINDR levels during therapeutic intervention.

In one aspect, hybridization with PCR probes which are capable of detecting polynucleotide sequences, including genomic sequences, encoding BINDR or closely related molecules, may be used to identify nucleic acid sequences which encode BINDR. The specificity of the probe, whether it is made from a highly specific region, e.g., 10 unique nucleotides in the 5' regulatory region, or a less specific region e.g., especially in the 3' coding region, and the stringency of the hybridization or amplification (maximal, high, intermediate, or low) will determine whether the probe identifies only naturally occurring sequences encoding BINDR, alleles, or related sequences.

Probes may also be used for the detection of related sequences, and should preferably contain at least 50% of the nucleotides from any of the BINDR encoding sequences. The hybridization probes of the subject invention may be DNA or RNA and derived from the nucleotide sequence of SEQ ID NO:2 or from genomic sequence including promoter, enhancer elements, and introns of the naturally occurring BINDR.

Means for producing specific hybridization probes for DNAs encoding BINDR include the cloning of nucleic acid sequences encoding BINDR or BINDR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding BINDR may be used for the diagnosis of disorders which are associated with expression of BINDR. Examples of such conditions or diseases include, but are not limited to, cancers such as adenocarcinoma, leukemia, lymphoma, melanoma, myeloma, sarcoma, and teratocarcinoma and particularly cancers of the adrenal gland, bladder, bone, brain, breast, cervix, gall bladder, gastrointestinal tract, heart, kidney, liver, lung, ovaries, pancreas, paragangliomas, parathyroid, pituitary gland, prostate, salivary gland, spleen, stomach, thymus, thyroid, testes, and uterus. The polynucleotide sequences encoding BINDR may be used in Southern or northern analysis, dot blot, or other membrane-based technologies; in PCR technologies; or in dip stick, pin, ELISA or chip assays utilizing fluids or tissues from patient biopsies to detect altered BINDR expression. Such qualitative or quantitative methods are well known in the art.

In a particular aspect, the nucleotide sequences encoding BINDR may be useful in assays that detect activation or induction of various cancers, particularly those mentioned above. The nucleotide sequences encoding BINDR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding BINDR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of BINDR, a normal or standard profile for expression is established. This may be accomplished by combining body fluids or cell extracts taken from normal subjects, either animal or human, with a sequence, or a fragment thereof, which encodes BINDR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding BINDR may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of BINDR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences which encode BINDR may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding BINDR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, BINDR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between BINDR and the agent being tested, may be measured.

Another technique for drug screening which may be used provides for high throughput screening of compounds having suitable binding affinity to the protein of interest as described in published PCT application WO84/03564. In this method, as applied to BINDR large numbers of different small test compounds are synthesized on a solid substrate, such as plastic pins or some other surface. The test compounds are reacted with BINDR, or fragments thereof, and washed. Bound BINDR is then detected by methods well known in the art. Purified BINDR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding BINDR specifically compete with a test compound for binding BINDR. In this manner, the antibodies can be used to detect the presence of any peptide which shares one or more antigenic determinants with BINDR.

In additional embodiments, the nucleotide sequences which encode BINDR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES
I cDNA Library Construction
The PGANNOT01 cDNA library was constructed from paraganglion tissue obtained from a 46 year-old male. The frozen tissue was homogenized and lysed in guanidinium isothiocyanate solution using a Brinkmann Homogenizer Polytron PT-3000 (Brinkmann Instruments, Westbury N.J.). The lysate was centrifuged over a 5.7M CsCl cushion using a Beckman SW28 rotor in a Beckman L8-70M Ultracentrifuge (Beckman Instruments) for 18 hours at 25,000 rpm at ambient temperature. The RNA was extracted twice with acid phenol pH 4.0 following Stratagene's RNA isolation protocol, precipitated using 0.3M sodium acetate and 2.5 volumes of ethanol, resuspended in DEPC-treated water, and DNase treated for 15 min at 37° C. The reaction was stopped with an equal volume of acid phenol and the RNA was isolated with the Qiagen OLIGOTEX kit and used to construct the cDNA library.

The RNA was handled according to the recommended protocols in the SuperScript Plasmid System for cDNA Synthesis and Plasmid Cloning (catalog #18248-013; Gibco/BRL), and cDNAs were ligated into PSPORT1. The plasmid PSPORT1 was subsequently transformed into DH5a competent cells (Cat. #18258-012, Gibco/BRL).

II Isolation of cDNA Clones
Plasmid DNA was released from the cells and purified using the Miniprep Kit (Catalogue #77468; Advanced Genetic Technologies Corporation, Gaithersburg, Md.). This kit consists of a 96 well block with reagents for 960 purifications. The recommended protocol was employed except for the following changes: 1) the 96 wells were each filled with only 1 ml of sterile Terrific Broth (Catalog #22711, GIBCO/BRL) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs for the library were sequenced by the method of Sanger, F. and Coulson, A. R. (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc Nat. Acad. Sci. 90:5893-3) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide). Product score, the calculation of which is shown below, was used to determine the electronic stringency. For an exact match, product score was set at 70 with a conservative lower limit set at approximately 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding BINDR occurs. Abundance and percent abundance are also reported. Abundance directly reflects the number of times a particular transcript is represented in a cDNA library, and percent abundance is abundance divided by the total number of sequences examined in the cDNA library.

V Extension of BINDR-Encoding Polynucleotides

Nucleic acid sequence of Incyte clone 620438 or SEQ ID NO:2 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermnal Cycler (PTC200; M. J. Research, Watertown, Mass.) and the following parameters:

| Step | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 μl of liquid LB/2× Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VIII Complementary Polynucleotides

Sequence complementary to the BINDR-encoding sequence, or any part thereof, is used to decrease or inhibit expression of naturally occurring BINDR. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of BINDR, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the BINDR-encoding transcript.

VIII Expression of BINDR

Expression of BINDR is accomplished by subcloning the cDNAs into appropriate vectors and transforming the vectors into host cells. In this case, the cloning vector is used to express BINDR in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of BINDR into the bacterial growth media which can be used directly in the following assay for activity.

IX Demonstration of BINDR Activity

BINDR can be expressed by transforming a mammalian cell line such as COS7, HeLa or CHO with an eukaryotic expression vector encoding BINDR. Eukaryotic expression vectors are commercially available, and the techniques to introduce them into cells are well known to those skilled in the art. The cells are incubated for 48–72 hours after transformation under conditions appropriate for the cell line to allow expression and accumulation of BINDR.

Extracts containing solubilized proteins can be prepared from cells expressing BINDR by methods well known in the art. These extracts are used to demonstrate the double-stranded RNA-binding activity of BINDR. Portions of the extract containing BINDR are added to an amount of a [$^{32}$P]-labeled double-stranded RNA. To prepare the double-stranded RNA substrates, poly(rI) and poly(rC) (Pharmacia Biotech Inc.) are partially hydrolyzed in 100 mM sodium carbonate buffer, pH 10.2, at 70° C. for 40 min to produce an average fragment size of 50 nucleotides. T4 polynucleotide kinase is used to end label 10 $\mu$g of rI and rC with [−32P]ATP (6000 Ci/mmol, 10 $\mu$Ci/$\mu$l). Labeled RNAs are annealed by heating to 70° C., slowly cooled, then purified over a SEPHADEX G-10 column. The mixtures of BINDR are incubated at 25° C. in the presence of RNase inhibitors, under suitable conditions of ionic strength and pH, for 5–10 minutes. Appropriate control samples are prepared using extracts of untransformed cells and/or cells transformed with vector sequences alone.

After incubation, the samples are applied to the wells of a polyacrylamide gel and electrophoresed at constant current until a suitable tracking dye, such as xylene cyanol FF (Sigma) has migrated to the bottom of the gel. The gel is exposed against Kodak XOMAT AR film (Kodak) for a suitable period of time.

A band will be visible on the film at a position that is indicative of a complex formed between BINDR and the radioactive double-stranded transcript. A band of similar mobility will not be present in samples prepared using control extracts prepared from untransformed cells or cells transformed with vector sequence alone. The presence of BINDR in the complex may be confirmed using an antibody specific for BINDR. When added to the samples, the specific anti-BINDR antibody will bind to and decrease the electrophoretic mobility of the BINDR-RNA complex, thereby causing a new radioactive band to appear at a higher position in the gel. Pre-immune sera or unrelated antisera may be used as suitable controls for nonspecific binding to the complex.

X Production of BINDR Specific Antibodies

BINDR that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring BINDR Using Specific Antibodies

Naturally occurring or recombinant BINDR is substantially purified by immunoaffinity chromatography using antibodies specific for BINDR. An immunoaffinity column is constructed by covalently coupling BINDR antibody to an activated chromatographic resin, such as CnBr-activated SEPHAROSE (Pharmacia & Upjohn). After the coupling, the resin is blocked and washed according to the manufacturer's instructions.

Media containing BINDR is passed over the immunoaffinity column, and the column is washed under conditions that allow the preferential absorbance of BINDR (e.g., high ionic strength buffers in the presence of detergent). The column is eluted under conditions that disrupt antibody/BINDR binding (eg, a buffer of pH 2–3 or a high concentration of a chaotrope, such as urea or thiocyanate ion), and BINDR is collected.

XII Identification of Molecules Which Interact with BINDR

BINDR or biologically active fragments thereof are labeled with $^{125}I$ Bolton-Hunter reagent (Bolton et al. (1973) Biochem. J. 133: 529). Candidate molecules previously arrayed in the wells of a multi-well plate are incubated with the labeled BINDR, washed and any wells with labeled BINDR complex are assayed. Data obtained using different concentrations of BINDR are used to calculate values for the number, affinity, and association of BINDR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide consisting of the amino acid sequence of SEQ ID NO:1.

2. A hybridization probe comprising the polynucleotide of claim 1.

3. An isolated and purified polynucleotide consisting of the nucleic acid sequence of SEQ ID NO:2.

4. An isolated and purified polynucleotide which is completely complementary to the polynucleotide of claim 1.

5. A hybridization probe comprising the isolated and purified polynucleotide of claim 4.

6. An expression vector comprising the polynucleotide of claim 1.

7. A host cell comprising the expression vector of claim 6.

8. A method for detection of a polynucleotide encoding a polypeptide consisting of the amino acid sequence of SEQ ID NO:1 in a biological sample containing nucleic acid material, the method comprising the steps of:

a) hybridizing the polynucleotide of claim 5 to the nucleic acid material of the biological sample, thereby forming a hybridization complex; and b) detecting the hybridization complex, wherein the presence of the complex correlates with the presence of the polynucleotide the polypeptide in the biological sample.

* * * * *

UNITED STATES PATENT AND TRADEMARK OFFICE
CERTIFICATE OF CORRECTION

PATENT NO. : 5,858,675
DATED : January 12, 1999
INVENTOR(S) : Hillman et al

It is certified that error appears in the above-identified patent and that said Letters Patent is hereby corrected as shown below:

Col. 42, line 34, delete "polynucleotide the" and insert --polynucleotide encoding the--.

Signed and Sealed this

Twentieth Day of June, 2000

Attest:

Q. TODD DICKINSON

*Attesting Officer*    *Director of Patents and Trademarks*